(12) United States Patent
Alonso Cohen et al.

(10) Patent No.: US 10,780,146 B2
(45) Date of Patent: Sep. 22, 2020

(54) COMPOSITIONS FOR THE TREATMENT OF INTESTINAL DISORDERS

(71) Applicant: NOVINTETHICAL PHARMA SA, Lugano (CH)

(72) Inventors: Miguel Angel Alonso Cohen, Barcelona (ES); Marco Di Fulvio, Soriano Nel Cimino (IT)

(73) Assignee: DEVINTEC SAGL, Lugano (CH)

( * ) Notice: Subject to any disclaimer, the term of this patent is extended or adjusted under 35 U.S.C. 154(b) by 0 days.

(21) Appl. No.: 16/099,289

(22) PCT Filed: May 8, 2017

(86) PCT No.: PCT/EP2017/060942
§ 371 (c)(1),
(2) Date: Nov. 6, 2018

(87) PCT Pub. No.: WO2017/207223
PCT Pub. Date: Dec. 7, 2017

(65) Prior Publication Data
US 2019/0209647 A1  Jul. 11, 2019

(30) Foreign Application Priority Data

May 31, 2016 (EP) ..................... 16172130
Jul. 14, 2016 (EP) ..................... 16179429

(51) Int. Cl.
| | |
|---|---|
| *A61K 38/16* | (2006.01) |
| *C07K 1/107* | (2006.01) |
| *A61K 47/61* | (2017.01) |
| *A61K 47/64* | (2017.01) |
| *A61K 38/01* | (2006.01) |
| *A61P 29/00* | (2006.01) |
| *A61P 1/04* | (2006.01) |
| *A61P 35/00* | (2006.01) |
| *A61K 9/00* | (2006.01) |

(52) U.S. Cl.
CPC .......... *A61K 38/168* (2013.01); *A61K 9/0053* (2013.01); *A61K 38/01* (2013.01); *A61K 38/011* (2013.01); *A61K 47/61* (2017.08); *A61K 47/64* (2017.08); *A61P 1/04* (2018.01); *A61P 29/00* (2018.01); *A61P 35/00* (2018.01); *C07K 1/1077* (2013.01)

(58) Field of Classification Search
None
See application file for complete search history.

(56) References Cited

FOREIGN PATENT DOCUMENTS

| WO | WO 2006/131262 A1 | 12/2006 |
|---|---|---|
| WO | WO 2015/158771 A1 | 10/2015 |

OTHER PUBLICATIONS

Yin et al. ("Influence of pea protein aggregates on the structure and stability of pea protein/soy bean polysaccharide complex emulsions" Molecules Mar. 2015, 20, 5165-5183).*
International Search Report and Written Opinion dated Jul. 24, 2017 for PCT Application No. PCT/EP2017/060942, 16 pages.
Aberkane, Leila, et al., "Encapsulation and oxidative stability of PUFA-Rich oil microencapsulated by spray drying using pea protein and pectin", Food Bioprocess Technol, Oct. 2013, vol. 7, pp. 1505-1517.
Bradley, Peter MD, et al., "Measurement of cutaneous inflammation: estimation of Neutrophil content with an enzyme marker", Journal Investigative Dermatology, 1982, vol. 78, No. 3, pp. 206-209.
Condratovici, Catalin Plesea, et al., "Xyloglucan for the treatment of acute gastroenteritis in children: results of a randomized, controlled, clinical trial", Gastroenterology Research and Practice, Mar. 2016, vol. 2016, Article ID 6874207, pp. 1-7.
Gnessi, Lucio, et al., "Xyloglucan for the treatment of acute diarrhea: results of a randomized, controlled, open-label, parallel group, multicenter, national clinical trial", BMC Gastroenterology, Oct. 2015, vol. 15:153, pp. 1-8.
Lahaye, Marc, et al., "Structure and functional properties of Ulvan, a polysaccharide from green seaweeds", Bio Macromolecules, Jun. 2007, vol. 8, No. 6, pp. 1765-1774.
Langeveld, Sandra M.J., et al., "Glucosylation activity and complex formation of two classes of reversibly glycosylated polypeptides", Plant Physiology, May 2002, vol. 129, pp. 278-289.
Ndiaye, Fatou, et al., "Anti-oxidant, anti-inflammatory and immunomodulating properties of an enzymatic protein hydrolysate from yellow field pea seeds", European Journal Nutr 2012, Mar. 27, 2011, vol. 51, pp. 29-37.
O;Sullivan, Laurie, et al., "Prebiotics from marine macroalgae for human and aninal health applications", Marine Drugs Jul. 2010, ISSN 1660-3397, vol. 8, pp. 2038-2064.
Ye, Yi N., et al., "A new role of heparin: a polysaccharide for gastrointestinal diseases", Inflammopharcacology NL, Dec. 1, 2002, vol. 10, No. 4-6, 10 pages.

* cited by examiner

*Primary Examiner* — Christina Bradley
(74) *Attorney, Agent, or Firm* — Squire Patton Boggs (US) LLP

(57) ABSTRACT

The invention provides a process for preparing a protein-polysaccharide conjugated product comprising: (a) preparing a mixture comprising pea protein, polysaccharide, and an appropriate polar solvent; wherein: the weight ratio between polysaccharide and protein is comprised from 20:80 to 60:40, and the pH of the solution is comprised from 8.0 to 10.5; and performing a Maillard reaction by heating the solution resulting from step (a) at an appropriate temperature for the necessary period of time to conjugate the protein and the polysaccharide. The invention further provides a conjugated product obtainable by the process of the invention, as well as pharmaceutical compositions comprising the conjugate and to their use in the treatment in gastrointestinal disorders. The conjugate of the invention shows a remarkable improvement in preventing and/or treating intestinal diseases, such as mucositis.

8 Claims, 4 Drawing Sheets

COMPOSITIONS FOR THE TREATMENT OF INTESTINAL DISORDERS

This application claims the benefit of European Patent Application EP16172130.3, filed on May 31, 2016, and EP16179429.2, filed on Jul. 14, 2016.

The invention relates to the field of medicine, in particular to the field of gastroenterology and, more particularly, to intestinal diseases. The present invention provides polysaccharide-protein conjugates showing a synergistic efficacy in protecting the intestinal tract against disorders such as entiritis.

BACKGROUND ART

The intestinal mucosa is the first layer of the gastrointestinal tract on the luminal side. This layer comes in direct contact with ingested food, and micro-organisms residing in the gut. Thus this layer is responsible for the important processes in digestion such as absorption, secretion and in barrier function.

The gastrointestinal mucosa comprises epithelial cells, which are held together with so called tight junctions.

The tight junction, also called zona occludens, is a specialized cell-cell interaction that is found in almost all types of epithelial cell lines in different organs in the body. Tight junctions are the closely associated areas of two adjacent cells whose membranes join together forming a virtually impermeable barrier to gastrointestinal contents. A tight junction comprises densely packed protein complexes that provide contact between the membranes of two adjacent cells.

One of the functions of tight junctions is regulating the passage of molecules and ions through the space between cells. The tight junction represents a major barrier for paracellular transport, i.e. transport through the intercellular spaces between epithelial cells, and may prevent such passage of molecules and ions. Consequently, materials must enter the epithelial cells, through e.g. diffusion or active transport, in order to pass through the tissue. This is called transcellular transport and such transport provides control over what substances are allowed through e.g. the intestinal mucosa. Epithelia are classed as 'tight' or 'leaky' depending on the ability of the tight junctions to prevent water and solute movement through intercellular space.

An important task of the intestine is to form a defensive barrier to prevent absorption of damaging substances from the external environment. This protective function is mainly dependent on the barrier properties of the intestinal mucosa. The permeability of the intestinal mucosa is determined at least in part by the strength of the tight junctions of the intestinal epithelial cells.

There are a number of factors that may affect tight junctions, including food components such as gluten and casein in some individuals. Infectious organisms such as specific pathogenic strains of *E. coli, Salmonella*, and *C. difficile* have the ability to disrupt the tight junction protein complexes between the epithelial cells and setting up an infection. Disruption of the tight junctions may result in lowering the barrier properties of the intestinal mucosal epithelium, leading to leaky gut.

Another common problem that also affects the gastrointestinal system is inflammation of the epithelial cell lining. Duodenitis is inflammation of the first part of the small intestine. A much more serious form of inflammation of the small or large intestine is inflammatory bowel disease ("IBD") characterized by gross inflammation that is out of control, an intestinal lining that bleeds and is ulcerated, and weight loss. Crohn's Disease is a form of IBD. Diverticular disease represents bacterial inflammation of the large intestine, and typically afflicts people who suffer from constipation.

Diseases of the intestine may cause vomiting, diarrhea or constipation, and altered stool, such as with blood in stool, among others.

In view of their different etiologies, various treatment options are available, based on the administration of antibiotics/antibacterial, spasmolytic/anticholinergics, probiotics, or opioid receptor agonists. However, some of said treatments must be administered with great caution, because they do not act on the causal pathological process.

In an attempt to prevent said adverse effects, complexes of tannins and animal proteins and gelatins, in particular with gelatin of bovine origin, albumin, casein or ovalbumin, have been proposed for some time.

Alternatively, WO2006131262 has disclosed a composition for use in the treatment of gastro-intestinal disorders or of disorders originating in the gastro-intestinal system and transferred to other systems, said composition comprising xyloglucans or extracts containing xyloglucans.

In an attempt to improve the efficacy of xyloglucan compositions, WO2015158771 has disclosed that mixing the xyloglucan with pea protein an improvement in the efficacy could be achieved when compared with xyloglucan alone.

In spite of the efforts made, however, there is still the need of compositions with improved efficacy in preventing the development of gastrointestinal diseases.

SUMMARY OF THE INVENTION

The present inventors have found that when a mixture of protein and a polysaccharide, such as xyloglucan, at a particular weight ratio and pH conditions, is subjected to a conjugation process through a Maillard reaction, a product having a remarkably improved effect in preventing and/or treating intestinal diseases is obtained.

As it is shown below, comparative data were generated using (a) mixtures of protein (pea protein) and polysaccharide (xyloglucan) at different weight ratios and (b) conjugates obtained after submitting mixtures (a) to Maillard reaction. The results allow concluding that a substantial reduction in gut permeability can be achieved when the protein and the polysaccharide are covalently bound by Maillard reaction in comparison with the corresponding mixture without conjugation (see Table 1, below).

In addition, as it is shown in Table 2 below, by conjugating the protein to the polysaccharide, a product having a more efficient prevention of jejuna mucosa inflammation is achieved when compared with the effect obtained using the corresponding mixture of both components without conjugation. In view of the remarkable improvement observed, it can be said that a synergistic effect occurs when protein and polysaccharide are conjugated.

The positive effect of the conjugation in preventing gastro-intestinal diseases was surprising since previous results obtained from mucoadhesive in-vitro tests showed that a 3-fold reduction in mucoadhesion occurred when protein was conjugated to the polysaccharide, in comparison with the polysaccharide alone (FIG. 1). That is, the covalent binding of the protein (in case of the conjugate), negatively affected xyloglucan's mucoadhesion. However, and contrary to what the skilled person in the art would expect in view of the mucoadhesive results, a remarkable improvement in gut permeability and inflammation prevention were found in in-vivo experiments carried out with the protein-polysaccharide conjugated product of the invention.

These in-vivo data suggests (1) the usability of the conjugate protein-polysaccharide in the treatment and/or prevention of gastrointestinal diseases and (2) that the remarkable improvement in the prevention of the disease is not due to the mucoadhesion property of polysaccharide (xyloglucan) but to a synergistic effect in the activity when protein is conjugated to the polysaccharide.

This conjugated product may be defined by its preparation process.

Thus, in a first aspect the present invention provides a process for preparing a protein-polysaccharide conjugated product comprising:

(a) preparing a mixture comprising pea protein, polysaccharide, and an appropriate polar solvent; wherein:
  the weight ratio between polysaccharide and pea protein is comprised from 20:80 to 60:40, and
  the pH of the solution is comprised from 8.0 to 10.5; and
(b) performing a Maillard reaction by heating the solution resulting from step (a) at an appropriate temperature for the necessary period of time to conjugate the protein and the polysaccharide.

Taken together the results provided below, the conjugation of polysaccharide and protein by Maillard reaction, at specific weight ratios and pH conditions, provides protein-polysaccharide conjugates with the ability of inducing a strong protective effect by forming a thicker covering the intestinal barrier, which is independent of the mucoadhesive properties.

In a second aspect the present invention provides a protein-polysaccharide conjugated product obtainable by the process of the first aspect of the invention.

In a third aspect, the present invention provides a pharmaceutical or veterinary composition comprising a therapeutically effective amount of the protein-polysaccharide conjugated product as defined in the second aspect of the invention together with one or more pharmaceutically or veterinary acceptable excipients or carriers.

In a fourth aspect, the present invention provides a nutraceutical composition comprising the protein-polysaccharide conjugated product as defined in the second aspect of the invention.

The present inventors carried out a test with *E. coli*-induced enteritis in rats. Some rats, prior to the induction of the disease, were orally administered the conjugate of the invention. The results provided below illustrates that the conjugate of the invention confers a strong protective effect due a remarkably reduction in gut permeability. Furthermore, the results provided in Table 2 below also illustrates that the inflammation of jejuna mucosa, characteristic of many intestinal diseases such as IBD diseases, can also be substantially prevented with the protein-polysaccharide conjugated product of the present invention.

Altogether, the experimental data supports the use of the conjugate of the invention as a medicament. And that other proteins and mucoadhesive polysaccharides can be conjugated via Maillard reaction to get the same synergistic effect in the prevention or treatment of gastrointestinal diseases.

Therefore, in a fifth aspect the present invention provides a protein-polysaccharide conjugated product as defined in the second aspect of the invention, for use as a medicament.

In a sixth aspect the present invention provides a pea protein-polysaccharide conjugated product as defined in the second aspect of the invention, for use in the prevention and/or treatment of gastrointestinal disorders. This aspect can be alternatively formulated as the use of a pea protein-polysaccharide conjugated product as defined in the second aspect of the invention for the manufacture of a medicament for the prevention and/or treatment of intestinal disorders. This aspect can also be alternatively formulated as a method for the prevention and/or treatment of an intestinal disorder, the method comprising administering, to a subject in need thereof, a therapeutically effective amount of the pea protein-polysaccharide conjugated product as defined in the second aspect of the invention.

And, finally, in a seventh aspect, the present invention provides a protein-xyloglucan conjugated product for use in the prevention and/or treatment of gastrointestinal disorders, wherein the protein-polysaccharide conjugated product is obtainable by a process comprising the steps of:

(A) preparing a mixture comprising protein, polysaccharide, and an appropriate polar solvent, wherein
  the weight ratio between the polysaccharide and the protein is comprised from 20:80 to 60:40, and
  the pH of the solution is comprised from 8.0 to 10.5, and
(B) performing a Maillard reaction by heating the solution resulting from step (A) at an appropriate temperature for the necessary period of time to conjugate the protein and the polysaccharide.

This seventh aspect can be alternatively formulated as the use of a protein-polysaccharide conjugated product obtainable by a process comprising steps (A) to (C) above for the manufacture of a medicament for the prevention and/or treatment of intestinal disorders. This aspect can be alternatively formulated as a method for preventing and/or treating intestinal disorders, the method comprising administering an effective therapeutically amount of a protein-polysaccharide conjugated product obtainable by a process comprising steps (A) to (C) above, to a subject in need thereof.

As it is illustrated below, the inventors have also surprisingly found that the conjugated product of the invention, when administered with a chemotherapeutic agent, efficiently prevents the typical inflammation side-effect due to chemotherapy.

Thus, in an eighth aspect the present invention provides a protein-polysaccharide conjugated product as defined in the second aspect of the invention for use in combination therapy for the prevention or treatment of cancer, wherein the therapy comprises administering to a subject simultaneously, sequentially or separately the conjugated product and a chemotherapeutic agent.

In a ninth aspect, the present invention provides a combination of a protein-polysaccharide conjugated product as defined in the second aspect of the invention and a chemotherapeutic agent, for use in the prevention or treatment of cancer.

In a tenth aspect the present invention provides a protein-polysaccharide conjugated product as defined in the second aspect of the invention for use in the combination therapy with a chemotherapeutic agent, wherein the use comprises the prevention and/or treatment of an intestinal mucosa inflammatory disorder.

In a final aspect the present invention provides a chemotherapeutic agent for use in combination therapy with the protein-polysaccharide conjugated product as defined in the second aspect of the invention, wherein the use comprises the prevention or treatment of cancer.

DETAILED DESCRIPTION OF THE INVENTION

Figure 1:
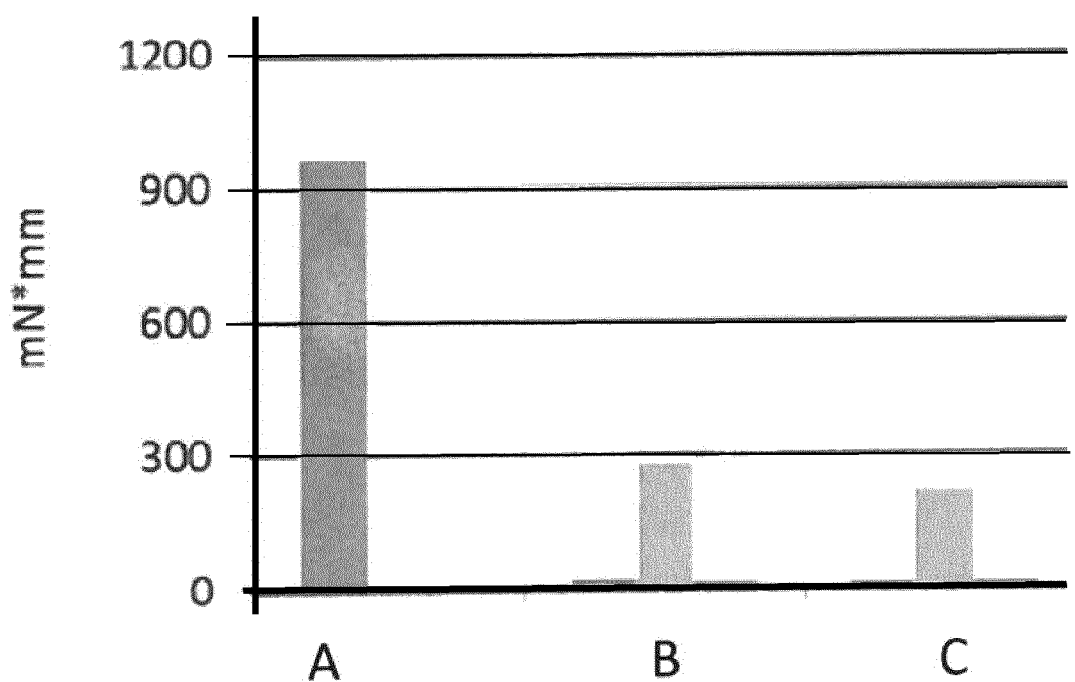
FIG. 1 represents the mucoadhesion work (expressed in mN*mm) for xyloglucan alone (a), for a conjugate xyloglucan:pea protein of the invention at a weight ratio 50:50 (b), and for a conjugate of the invention xyloglucan:pea protein:pea protein at a weight ratio 30:70 (c).

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For purposes of the present invention, any ranges given include both the lower and the upper end-points of the range. Ranges given, such as concentrations, temperatures, times, and the like, should be considered approximate, unless specifically stated.

In a first aspect the present invention provides a process for obtaining the conjugate of the first aspect of the invention.

In the present invention, the term "polysaccharide" refers to a polymeric carbohydrate molecule composed of long chains of monosaccharide units bound together by glycosidic linkages and on hydrolysis give the constituent monosaccharides or oligosaccharides. They range in structure from linear to highly branched. Examples include storage polysaccharides such as starch and glycogen, and structural polysaccharides such as cellulose and chitin. In the context of the invention, the polysaccharide is mucoadhesive, i.e., that it adheres on mucous membrane. There are well-known tests for measuring the mucoadhesion of a polysaccharide such as the one provided below, in the section of Examples, based on the work of mucoadhesion.

In one embodiment of the first aspect of the invention, optionally in combination with any of the embodiments provided below, the polysaccharide is xyloglucan, fucoidan or ulvans.

In the present invention, the term "xyloglucan" refers to a backbone of β1→4-linked glucose residues, most of which are substituted with 1-6 linked xylose sidechains. The xylose residues are often capped with a galactose residue sometimes followed by a fucose residue. Xyloglucan has the CAS number 37294-28-3.

A particularly rich source of xyloglucan is the seed of the tamarind (*Tamarindus indica*), a tropical tree from East Africa. Xyloglucans extracts from *Tamarindus indica* are available in the market from example from Indena (Italy) (Xilogel®), Megazyme, and from DSP Gokyo Food & Chemical (Japan) (Glyloid®).

In the present invention the term "fucoidan" refers to a sulfated polysaccharide that have a backbone built of (1→3)-linked α-l-fucopyranosyl or of alternating (1→3)- and (1→4)-linked α-l-fucopyranosyl residues, but also include sulfated galactofucans with backbones built of (1→6)-β-d-galacto- and/or (1→2)-β-d-mannopyranosyl units with fucose or fuco-oligosaccharide branching, and/or glucuronic acid, xylose or glucose substitutions (MW: average 20,000), found mainly in various species of brown algae and brown seaweed such as mozuku, kombu, bladderwrack, wakame, and hijiki (variant forms of fucoidan have also been found in animal species, including the sea cucumber).

In the present invention the term "ulvan" refers to a polysaccharide derived from *Ulva lactuca*. This polysaccharide has been deeply characterised in the state of the art (Audrey R. et al., "Structure and Functional Properties of Ulvan, a Polysaccharide from Green Seaweeds", 2007, American Chemical Society, 8(6), 1765-1774).

In the present invention, the term "pea protein" is the generic name given to any protein isolate obtained from yellow pea, *Pisum sativum*, seeds. "Pea protein" contains Legumin, which has some similar properties to Casein, and pea protein products are promoted as an alternative to whey protein. "Pea protein" is worldwide sold under different trademarks such as, Nutralys®, and P80X, among others. And it can also be prepared from pea cultivars by well-known routine methods, such as alkali extraction/isoelectric precipitation (AE-IP), salt extraction-dialysis (SE), and micellar precipitation (MP), among others.

The term "weight ratio" refers to the relation of weights of polysaccharide:pea protein.

As it has been mentioned above, the mixture of xyloglucan and protein is submitted to Maillard reaction. Maillard reaction comprises three main stages:

Scheme 1

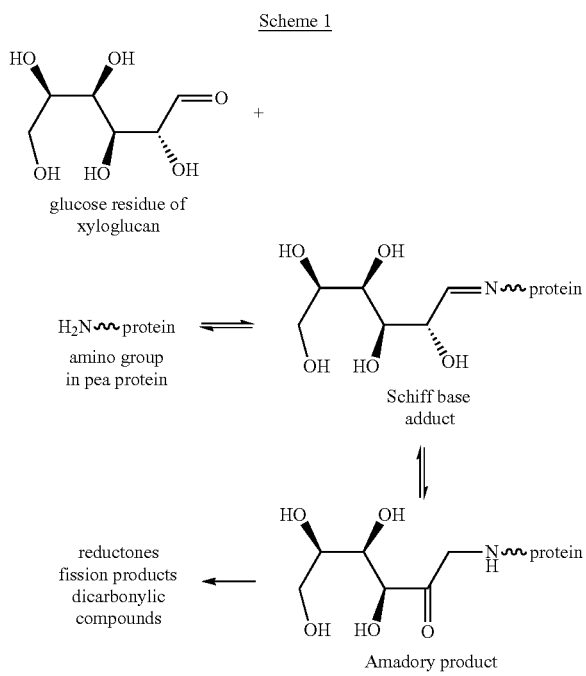

Briefly, (1) the carbonyl group on sugar (i.e., polysaccharide) reacts with a protein amino group by heating, thus producing a N-substituted glycosylamine; (2) the Schiff base adduct isomerases, giving Amadory product ketosamine. In a final step, Amadori product, under the specific reaction conditions of temperature and pH, can give rise to the formation of further products, such as reductones or fission products.

In one embodiment of the first aspect of the invention, optionally in combination with one or more of the embodiments described above or below, step (a) comprises the steps of:
(a.1) dissolving the pea protein in the appropriate polar solvent,
(a.2) adjusting the pH of the solution to a pH value comprised from 8.0 to 10.5, and
(a.3) adding the polysaccharide to the solution resulting from step (a.2);
or, alternatively,
(a.I) mixing the pea protein and the polysaccharide in the appropriate polar solvent, and
(a.II) adjusting the pH of the solution to a pH value comprised from 8.0 to 10.5;
or, alternatively,
(a.i) dissolving polysaccharide in the appropriate polar solvent,
(a.ii) dissolving pea protein in the appropriate polar solvent, and
(a.iii) mixing the solutions from steps (a.i) and (a.ii),
the adjustment of the pH being performed in step (a.ii), once dissolved the pea protein, or, alternatively, after step (a.iii), once solutions from steps (a.i) and (a.ii) are mixed.

In another embodiment of the first aspect of the invention, optionally in combination with one or more of the embodiments provided above or below, step (a) is performed at room temperature.

In one embodiment of the first aspect of the invention, optionally in combination with one or more of the embodiments described above or below, the polar solvent is selected from the group consisting of: water, $(C_1$-$C_6)$alkyl-OH, $(C_1$-$C_6)$alkyl-C(O)—$(C_1$-$C_6)$alkyl, $(C_1$-$C_6)$alkyl-C(O)H, dimethylformamide, and any mixture thereof. Examples of appropriate $(C_3$-$C_6)$cyclic ethers include tetrahydrofurane and dioxane. In another embodiment of the first aspect of the invention, optionally in combination with one or more embodiments provided above or below, the polar solvent is water.

The term $(C_1$-$C_6)$ alkyl refers to a saturated straight or branched alkyl chain having from 1 to 4 carbon atoms. Illustrative non-limitative examples are: methyl, ethyl, propyl, isopropyl, butyl, isobutyl, sec-butyl, and tert-butyl.

In another embodiment of the first aspect of the invention, optionally in combination with one or more of the embodiments described above or below, the weight ratio polysaccharide:pea protein is comprised in the range from 30:70 to 60:40. In another embodiment of the first aspect of the invention, optionally in combination with one or more of the embodiments described above or below, the weight ratio polysaccharide:pea protein is comprised in the range from 30:70 to 50:50. In another embodiment of the first aspect of the invention, optionally in combination with one or more of the embodiments described above or below, the weight ratio polysaccharide:pea protein is 30:70. Remarkably, when the weight ratio xyloglucan and protein, with respect to the total weight of the final mixture in step (a), was 30:70, it was found a 3-fold reduction in gut permeability.

In another embodiment of the first aspect of the invention, optionally in combination with one or more of the embodiments described above or below, the weight ratio xyloglucan:pea protein is comprised in the range from 30:70 to 60:40. In another embodiment of the first aspect of the invention, optionally in combination with one or more of the embodiments described above or below, the weight ratio xyloglucan:pea protein is comprised in the range from 30:70 to 50:50. In another embodiment of the first aspect of the invention, optionally in combination with one or more of the embodiments described above or below, the weight ratio xyloglucan:pea protein is 30:70.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 8.0 to 10.5, and (a.3) adding the polysaccharide to the solution resulting from step (a.2); the weight ratio between polysaccharide and pea protein being comprised from 30:70 to 60:40.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 8.0 to 10.5, and (a.3) adding the xyloglucan to the solution resulting from step (a.2); the weight ratio between xyloglucan and pea protein being comprised from 30:70 to 60:40.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 8.0 to 10.5, and (a.3) adding the polysaccharide to the solution resulting from step (a.2); the weight ratio between polysaccharide and pea protein being 30:70.

In another embodiment of the first aspect of the invention, optionally in combination with one or more of the embodiments provided above or below, step (a) is performed by:

(a.1) dissolving the pea protein in water, (a.2) adjusting the pH of the solution to a pH value comprised from 8.0 to 10.5, and (a.3) adding the xyloglucan to the solution resulting from step (a.2); the weight ratio between xyloglucan:pea protein being 30:70.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 8.0 to 10.5, and (a.3) adding the polysaccharide to the solution resulting from step (a.2); the weight ratio between polysaccharide and pea protein being 50:50.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 8.0 to 10.5, and (a.3) adding the xyloglucan to the solution resulting from step (a.2); the weight ratio between pea protein and xyloglucan being 50:50.

In another embodiment of the first aspect of the invention, optionally in combination with one or more embodiments provided above or below, the pH of the solution is adjusted to a value comprised from 9.5 to 10.5.

In another embodiment of the first aspect of the invention, optionally in combination with one or more embodiments provided above or below, the pH of the solution is adjusted to 10.0.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the polysaccharide to the solution resulting from step (a.2); the weight ratio between polysaccharide and pea protein being comprised from 30:70 to 60:40.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the xyloglucan to the solution resulting from step (a.2); the weight ratio between xyloglucan and pea protein being comprised from 30:70 to 60:40.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the polysaccharide to the solution resulting from step (a.2); the weight ratio between polysaccharide and pea protein being 30:70.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the xyloglucan to the solution resulting from step (a.2); the weight ratio between xyloglucan and pea protein being 30:70.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the polysaccharide to the solution resulting from step (a.2); the weight ratio between pea protein and polysaccharide being 50:50.

In another embodiment of the first aspect of the invention, optionally in combination with one or more of the embodiments provided above or below, step (a) is performed by: (a.1) dissolving the pea protein in water, (a.2) adjusting the pH of the solution to a pH value comprised from 9.5 to 10.5, and (a.3) adding the xyloglucan to the solution resulting from step (a.2); the weight ratio between pea protein and xyloglucan being 50:50.

In order to adjust the pH of the mixture protein, polysaccharide and polar solvent, any appropriate base can be added, such as an alkali metal or alkaline earth metal hydroxides. Illustrative non-limitative examples are NaOH, KOH, $Ca(OH)_2$, among others.

In another embodiment of the first aspect of the invention, optionally in combination with one or more embodiments provided above or below, the pH is adjusted to 10.0 by adding NaOH.

In another embodiment of the first aspect of the invention, optionally in combination with one or more embodiments provided above or below, the weight ratio of polysaccharide:pea protein is 30:70 or 50:50, and the process comprises the steps of:
(i) mixing the pea protein with water;
(ii) adjusting the pH of the solution resulting from step (i) to a value of 9.5 to 10.5;
(iii) adding the polysaccharide to the solution resulting from step (ii); and
(iv) performing Maillard reaction by heating the solution resulting from step (iii) at a temperature comprised from 30 to 190° C. for the necessary period of time to conjugate the protein and the polysaccharide.

In another embodiment of the first aspect of the invention, optionally in combination with one or more embodiments provided above or below, the weight ratio of xyloglucan:pea protein is 30:70 or 50:50, and the process comprises the steps of:
(i) mixing the pea protein with water;
(ii) adjusting the pH of the solution resulting from step (i) to a value of 9.5 to 10.5;
(iii) adding the xyloglucan to the solution resulting from step (ii); and
(iv) performing Maillard reaction by heating the solution resulting from step (iii) at a temperature comprised from 30 to 190° C. for the necessary period of time to conjugate the protein and the xyloglucan.

In another embodiment of the first aspect of the invention, optionally in combination with one or more embodiments provided above or below, step (b) can be performed heating the mixture resulting from step (a) at a temperature comprised from 30 to 190° C. for the necessary period of time to obtain the conjugate. In another embodiment of the first aspect of the invention, optionally in combination with one or more embodiments provided above or below, step (b) can be performed heating the mixture resulting from step (a) at a temperature comprised from 35 to 170° C. for the necessary period of time to obtain the conjugate. In another embodiment of the first aspect of the invention, optionally in combination with one or more embodiments provided above or below, step (b) can be performed heating the mixture resulting from step (a) at a temperature comprised from 155 to 165° C. for the necessary period of time to obtain the conjugate. In another embodiment of the first aspect of the invention, optionally in combination with one or more embodiments provided above or below, step (b) can be performed heating the mixture resulting from step (a) at a temperature of 160° C. for the necessary period of time to obtain the conjugate.

In another embodiment of the first aspect of the invention, optionally in combination with one or more embodiments provided above or below, step (b) can be performed heating the mixture resulting from step (a) at a temperature comprised from 30 to 190° C. until dryness. In another embodiment of the first aspect of the invention, optionally in combination with one or more embodiments provided above or below, step (b) can be performed heating the mixture resulting from step (a) at a temperature comprised from 35 to 170° C. until dryness. In another embodiment of the first aspect of the invention, optionally in combination with one or more embodiments provided above or below, step (b) can be performed heating the mixture resulting from step (a) at a temperature comprised from 155 to 165° C. until dryness. In another embodiment of the first aspect of the invention, optionally in combination with one or more embodiments provided above or below, step (b) can be performed heating the mixture resulting from step (a) at a temperature of 160° C. until dryness.

Step (b) can be performed heating the mixture resulting from step (a) in an apparatus such as an oven or an atomizer, among others. Depending on the apparatus used for performing step (b), the conditions of temperature and time can be different.

Optionally, once the pH of the mixture has been adjusted and prior to step (b) (Maillard reaction), the mixture can be lyophilized. Performing Maillard reaction with the alkaline mixture previously lyophilized can improve the cross-linking efficiency between protein and polysaccharide.

In one embodiment of the first aspect of the invention, the process comprises the steps of: (a) preparing a mixture comprising pea protein, polysaccharide and water, the weight ratio between polysaccharide and pea protein being 30:70 or 50:50, and the pH of the solution being comprised from 9.5 to 10.5, and (b) performing Maillard reaction by heating the solution resulting from step (a) at a temperature comprised from 35 to 190° C.

In one embodiment of the first aspect of the invention, the process comprises the steps of: (a) preparing a mixture comprising pea protein, xyloglucan and water, the weight ratio between xyloglucan and pea protein being 30:70 or 50:50, and the pH of the solution being comprised from 9.5 to 10.5, and (b) performing Maillard reaction by heating the solution resulting from step (a) at a temperature comprised from 35 to 190° C.

In one embodiment of the first aspect of the invention, the process comprises the steps of: (a) preparing a mixture comprising pea protein, polysaccharide, and water, the weight ratio between polysaccharide and pea protein being 30:70 or 50:50, and the pH of the solution is 10, and (b) performing Maillard reaction by heating the solution resulting from step (a) at a temperature comprised from 35 to 190° C.

In one embodiment of the first aspect of the invention, the process comprises the steps of: (a) preparing a mixture comprising pea protein, xyloglucan, and water, the weight ratio between xyloglucan and pea protein being 30:70 or 50:50, and the pH of the solution is 10, and (b) performing Maillard reaction by heating the solution resulting from step (a) at a temperature comprised from 35 to 190° C.

In one embodiment of the first aspect of the invention, the process comprises the steps of: (a) preparing a mixture comprising pea protein, polysaccharide, and water, the weight ratio between polysaccharide and pea protein being 30:70 or 50:50, and the pH of the solution being comprised from 9.5 to 10.5, and (b) performing Maillard reaction by heating the solution resulting from step (a) at a temperature comprised from 155 to 165° C.

In one embodiment of the first aspect of the invention, the process comprises the steps of: (a) preparing a mixture comprising pea protein, xyloglucan, and water, the weight ratio between xyloglucan and pea protein being 30:70 or 50:50, and the pH of the solution being comprised from 9.5 to 10.5, and (b) performing Maillard reaction by heating the solution resulting from step (a) at a temperature comprised from 155 to 165° C.

In one embodiment of the first aspect of the invention, the process comprises the steps of: (a) preparing a mixture comprising pea protein, polysaccharide, and water, the weight ratio between polysaccharide and pea protein being 30:70 or 50:50 and the pH of the solution being 10, and (b) performing Maillard reaction by heating the solution resulting from step (a) at a temperature comprised from 155 to 165° C.

In one embodiment of the first aspect of the invention, the process comprises the steps of: (a) preparing a mixture comprising pea protein, xyloglucan, and water, the weight ratio between xyloglucan and pea protein being 30:70 or 50:50 and the pH of the solution being 10, and (b) performing Maillard reaction by heating the solution resulting from step (a) at a temperature comprised from 155 to 165° C.

In one embodiment of the first aspect of the invention, the process comprises the steps of: (a) preparing a mixture comprising pea protein, polysaccharide, and water, the weight ratio between polysaccharide and pea protein being 30:70 or 50:50 and the pH of the solution being comprised from 9.5 to 10.5, and (b) performing Maillard reaction by heating the solution resulting from step (a) at a temperature of 160° C.

In one embodiment of the first aspect of the invention, the process comprises the steps of: (a) preparing a mixture comprising pea protein, xyloglucan, and water, the weight ratio between xyloglucan and pea protein being 30:70 or 50:50 and the pH of the solution being comprised from 9.5 to 10.5, and (b) performing Maillard reaction by heating the solution resulting from step (a) at a temperature of 160° C.

In one embodiment of the first aspect of the invention, the process comprises the steps of: (a) preparing a mixture comprising pea protein, polysaccharide, and water, the weight ratio between polysaccharide and pea protein being 30:70 or 50:50 and the pH of the solution being 10, and (b) performing Maillard reaction by heating the solution resulting from step (a) at a temperature of 160° C.

In one embodiment of the first aspect of the invention, the process comprises the steps of: (a) preparing a mixture comprising pea protein, xyloglucan, and water, the weight ratio between xyloglucan and pea protein being 30:70 or 50:50 and the pH of the solution being 10, and (b) performing Maillard reaction by heating the solution resulting from step (a) at a temperature of 160° C.

In a second aspect, the present invention provides a pea protein-xyloglucan conjugated product obtainable by the process of the first aspect of the invention and any of the particular embodiments provided above for this process.

All the embodiments provided above as "embodiments of the first aspect of the invention" are also embodiments of the product of the second aspect of the invention, as being the product defined in terms of the process for its preparation.

The term "protein-polysaccharide conjugated product" obtainable by the process is used herein for defining the conjugate by its preparation process and refers to the product that can be obtained through the preparation process which comprise the indicated steps as herein defined. For the purposes of the invention, the expressions "obtainable", "obtained" and similar equivalent expressions are used interchangeably and, in any case, the expression "obtainable" encompasses the expression "obtained".

In a third aspect, the present invention provides a veterinary or pharmaceutical composition comprising the conjugate of the first aspect of the invention.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio. Likewise, the term "veterinary acceptable" means suitable for use in contact with a non-human animal. Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically or veterinary acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavoring agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

The pharmaceutical or veterinary composition of the invention can include other active ingredients, such as antibiotics, antimotility agents, steroidal or non-steroidal anti-inflammatories, compounds for the treatment of gastrointestinal meteorism (simethicone and the like), mesalazine, sucralfate, natural and synthetic polysaccharides such as for example pectines, chitosan (animal or vegetable), hyaluronic acid, Guar gum, xanthan gum, animal gelatins, other vegetable proteins such as whey protein, cellulose and hemicellulose and derivatives such as for example hydroxypropyl cellulose, carragenines, carbomers, cross-linking/polymerising compounds such as ferulic acid; polyphenols, such as for example gall polyphenols, grape seed polyphenols, probiotics, such as for example Lactobacilli, Bifidobacteria, yeasts and the like; and chemotherapeutic agents.

Alternatively, the pharmaceutical or veterinary composition of the present invention can be administered in combination with another medicament such as an antibiotic, an antimotility agent, a steroidal o non-steroidal anti-inflammatory, a probiotic, a compound for the treatment of gastrointestinal meteorism, such as mesalazine and sucralfate, or a chemotherapeutic agent. In this embodiment, the pharmaceutical or veterinary composition of the present invention and the "other medicament" can be administered simultaneously or sequentially.

In one embodiment of the third aspect of the invention, the pharmaceutical composition is an oral composition.

In a fourth aspect, the present invention provides a nutraceutical composition.

As used in the present invention, the term "nutraceutical" refers to any substance that is a food or a part of a food, and provides medical or health benefits, including the prevention and treatment of disease. Such products may range from isolated nutrients, dietary supplements and specific diets to genetically engineered designer foods, herbal products and processed foods, such as cereals, soups and beverages. It is important to note that this definition applies to all categories of food and parts of food. This definition also includes a bio-engineered designer vegetable food, functional food or pharmafood.

As it has been stated above, the conjugate of the invention shows a remarkable preventive effect in terms of gut permeability and jejuna mucosa inflammation. These make the conjugates of the invention useful in the prevention and treatment of gastro-intestinal disorders and of disorders originating in the gastro-intestinal system and transferred to other systems, such as for example the genitourinary system.

In a seventh aspect, the present invention provides a protein-polysaccharide conjugated product for use in the prevention or treatment of intestinal disorders.

In the seventh aspect of the invention, the expression "protein" refers to any isolated protein of vegetal or animal origin with the ability of swelling in aqueous medium. Illustrative non-limitative examples are gelatin, albumin, ovalbumin, casein, pea protein and soya protein, among others.

In one embodiment of the seventh aspect of the invention, optionally in combination with any of the embodiments provided above or below, the protein is pea protein.

In another embodiment of the seventh aspect of the invention, optionally in combination with any of the embodiments provided above or below, the polysaccharide is xyloglucan, fucoidan or ulvan.

In another embodiment of the seventh aspect of the invention, optionally in combination with any of the embodiments provided above or below, the protein is pea protein and the polysaccharide is xyloglucan.

In one embodiment of the seventh aspect of the invention, optionally in combination with one or more of the embodiments described above or below, step (A) comprises the steps of:

(A.1) dissolving the protein in the appropriate polar solvent, (A.2) adjusting the pH of the solution to a pH value comprised from 8.0 to 10.5, and (A.3) adding the polysaccharide (such as xyloglucan) to the solution resulting from step (A.2);

or, alternatively, (A.I) mixing the protein and the polysaccharide (such as xyloglucan) in the appropriate polar solvent, and (A.II) adjusting the pH of the solution to a pH value comprised from 8.0 to 10.5;

or, alternatively, (A.i) dissolving the polysaccharide (such as xyloglucan) in the appropriate polar solvent, (A.ii) dissolving protein in the appropriate polar solvent, and (A.iii) mixing the solutions from steps (A.i) and (A.ii), the adjustment of the pH being performed in step (A.ii), once dissolved the protein, or, alternatively, after step (A.iii), once solutions from steps (A.i) and (A.ii) are mixed.

In another embodiment of the seventh aspect of the invention, optionally in combination with one or more of the embodiments provided above or below step (A) is performed at room temperature.

In one embodiment of the seventh aspect of the invention, optionally in combination with one or more of the embodiments described above or below, the polar solvent is selected from the group consisting of: water, $(C_1$-$C_6)$alkyl-OH, $(C_1$-$C_6)$alkyl-C(O)—$(C_1$-$C_6)$alkyl, $(C_1$-$C_6)$alkyl-C(O)H, dimethylformamide, and any mixture thereof. Examples of appropriate $(C_3$-$C_6)$cyclic ethers include tetrahydrofurane and dioxane. In another embodiment of the seventh aspect of the invention, optionally in combination with one or more embodiments provided above or below, the polar solvent is water.

The term $(C_1$-$C_6)$ alkyl refers to a saturated straight or branched alkyl chain having from 1 to 4 carbon atoms. Illustrative non-limitative examples are: methyl, ethyl, propyl, isopropyl, butyl, isobutyl, sec-butyl, and tert-butyl.

In another embodiment of the seventh aspect of the invention, optionally in combination with one or more of the embodiments described above or below, the weight ratio polysaccharide:protein is comprised in the range from 30:70 to 60:40. In another embodiment of the seventh aspect of the invention, optionally in combination with one or more of the embodiments described above or below, the weight ratio polysaccharide:protein is comprised in the range from 30:70 to 50:50. In another embodiment of the seventh aspect of the invention, optionally in combination with one or more of the embodiments described above or below, the weight ratio polysaccharide:protein is 30:70.

In another embodiment of the seventh aspect of the invention, optionally in combination with one or more of the embodiments described above or below, the weight ratio xyloglucan:protein is comprised in the range from 30:70 to 60:40. In another embodiment of the seventh aspect of the invention, optionally in combination with one or more of the embodiments described above or below, the weight ratio xyloglucan:protein is comprised in the range from 30:70 to 50:50. In another embodiment of the seventh aspect of the invention, optionally in combination with one or more of the embodiments described above or below, the weight ratio xyloglucan:protein is 30:70.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the polysaccharide to the solution resulting from step (A.2); the weight ratio between polysaccharide and protein being comprised from 30:70 to 60:40.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the xyloglucan to the solution resulting from step (A.2); the weight ratio between xyloglucan and protein being comprised from 30:70 to 60:40.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the polysaccharide to the solution resulting from step (A.2); the weight ratio between polysaccharide and protein being 30:70.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the xyloglucan to the solution resulting from step (A.2); the weight ratio between xyloglucan and protein being 30:70.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the polysaccharide to the solution resulting from step (A.2); the weight ratio between protein and polysaccharide being 50:50.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 8.0 to 10.5, and (A.3) adding the xyloglucan to the solution resulting from step (A.2); the weight ratio between protein and xyloglucan being 50:50.

In another embodiment of the seventh aspect of the invention, optionally in combination with one or more embodiments provided above or below, the pH of the solution is adjusted to a value comprised from 9.5 to 10.5.

In another embodiment of the seventh aspect of the invention, optionally in combination with one or more embodiments provided above or below, the pH of the solution is adjusted to 10.0.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the polysaccharide to the solution resulting from step (A.2); the weight ratio between polysaccharide and protein being comprised from 30:70 to 60:40.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the xyloglucan to the solution resulting from step (A.2); the weight ratio between xyloglucan and protein being comprised from 30:70 to 60:40.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the polysaccharide to the solution resulting from step (A.2); the weight ratio between polysaccharide and protein being 30:70.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the xyloglucan to the solution resulting from step (A.2); the weight ratio between xyloglucan and protein being 30:70.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the polysaccharide to the solution resulting from step (A.2); the weight ratio between protein and polysaccharide being 50:50.

In another embodiment of the seventh aspect of the invention, optionally in combination with one or more of the embodiments provided above or below, step (A) is performed by: (A.1) dissolving the protein in water, (A.2) adjusting the pH of the solution to a pH value comprised from 9.5 to 10.5, and (A.3) adding the xyloglucan to the solution resulting from step (A.2); the weight ratio between protein and xyloglucan being 50:50.

In order to adjust the pH of the mixture any appropriate base can be added, such as an alkali metal or alkaline earth metal hydroxides. Illustrative non-limitative examples are NaOH, KOH, $Ca(OH)_2$, among others.

In another embodiment of the seventh aspect of the invention, optionally in combination with one or more embodiments provided above or below, the pH is adjusted to 10.0 by adding NaOH.

In another embodiment of the seventh aspect of the invention, optionally in combination with one or more embodiments provided above or below, the weight ratio of polysaccharide:protein is selected from 30:70 and 50:50, and the process comprises the steps of:
  (I) mixing the protein with water;
  (II) adjusting the pH of the solution resulting from step (I) to a value of 9.5 to 10.5;
  (III) adding the polysaccharide to the solution resulting from step (II); and
  (IV) performing Maillard reaction by heating the solution resulting from step (III) at a temperature comprised from 140 to 190° C. for the necessary period of time to conjugate the protein and the polysaccharide.

In another embodiment of the seventh aspect of the invention, optionally in combination with one or more embodiments provided above or below, the weight ratio of xyloglucan:protein is selected from 30:70 and 50:50, and the process comprises the steps of:
  (I) mixing the protein with water;
  (II) adjusting the pH of the solution resulting from step (I) to a value of 9.5 to 10.5;

(III) adding the xyloglucan to the solution resulting from step (II); and (IV) performing Maillard reaction by heating the solution resulting from step (III) at a temperature comprised from 140 to 190° C. for the necessary period of time to conjugate the protein and the xyloglucan.

In another embodiment of the seventh aspect of the invention, optionally in combination with one or more embodiments provided above or below, step (B) can be performed heating the mixture resulting from step (A) at a temperature comprised from 30 to 190° C. for the necessary period of time to obtain the conjugate. In another embodiment of the seventh aspect of the invention, optionally in combination with one or more embodiments provided above or below, step (B) can be performed heating the mixture resulting from step (A) at a temperature comprised from 35 to 170° C. for the necessary period of time to obtain the conjugate. In another embodiment of the seventh aspect of the invention, optionally in combination with one or more embodiments provided above or below, step (B) can be performed heating the mixture resulting from step (A) at a temperature comprised from 155 to 165° C. for the necessary period of time to obtain the conjugate. In another embodiment of the seventh aspect of the invention, optionally in combination with one or more embodiments provided above or below, step (B) can be performed heating the mixture resulting from step (A) at a temperature of 160° C. for the necessary period of time to obtain the conjugate.

In another embodiment of the seventh aspect of the invention, optionally in combination with one or more embodiments provided above or below, step (B) can be performed heating the mixture resulting from step (A) at a temperature comprised from 30 to 190° C. until dryness. In another embodiment of the seventh aspect of the invention, optionally in combination with one or more embodiments provided above or below, step (B) can be performed heating the mixture resulting from step (A) at a temperature comprised from 35 to 170° C. until dryness. In another embodiment of the seventh aspect of the invention, optionally in combination with one or more embodiments provided above or below, step (B) can be performed heating the mixture resulting from step (A) at a temperature comprised from 155 to 165° C. until dryness. In another embodiment of the seventh aspect of the invention, optionally in combination with one or more embodiments provided above or below, step (B) can be performed heating the mixture resulting from step (A) at a temperature of 160° C. until dryness.

Step (B) can be performed heating the mixture resulting from step (A) in an apparatus such as an oven or an atomizer, among others. Depending on the apparatus used for performing step (B), the conditions of temperature and time can be different.

Optionally, once the pH of the mixture has been adjusted and prior to step (B) (Maillard reaction), the mixture can be lyophilized. Performing Maillard reaction with the alkaline mixture previously lyophilized can improve the cross-linking efficiency between protein and polysaccharide.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution being comprised from 9.5 to 10.5, and (B) performing Maillard reaction by heating the solution resulting from step (A) at a temperature comprised from 35 to 190° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution being comprised from 9.5 to 10.5, and (B) performing Maillard reaction by heating the solution resulting from step (A) at a temperature comprised from 35 to 190° C.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution is 10, and (B) performing Maillard reaction by heating the solution resulting from step (A) at a temperature comprised from 35 to 190° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution is 10, and (B) performing Maillard reaction by heating the solution resulting from step (A) at a temperature comprised from 35 to 190° C.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution being comprised from 9.5 to 10.5, and (B) performing Maillard reaction by heating the solution resulting from step (A) at a temperature comprised from 155 to 165° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution being comprised from 9.5 to 10.5, and (B) performing Maillard reaction by heating the solution resulting from step (A) at a temperature comprised from 155 to 165° C.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution is 10, and (B) performing Maillard reaction by heating the solution resulting from step (A) at a temperature comprised from 155 to 165° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution is 10, and (B) performing Maillard reaction by heating the solution resulting from step (A) at a temperature comprised from 155 to 165° C.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution being comprised from 9.5 to 10.5, and (B) performing Maillard reaction by heating the solution resulting from step (A) at a temperature of 160° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution being comprised from 9.5 to 10.5, and (B) performing Maillard reaction by heating the solution resulting from step (A) at a temperature of 160° C.

In one embodiment of the seventh aspect of the invention, the process comprises the steps of: (A) preparing a mixture of protein and polysaccharide in the presence of water, the weight ratio between polysaccharide and protein being 30:70 or 50:50 and the pH of the solution is 10, and (B) performing Maillard reaction by heating the solution resulting from step (A) at a temperature of 160° C.

In one embodiment of the seventh aspect of the invention, the process comprises the steps of: (A) preparing a mixture of protein and xyloglucan in the presence of water, the weight ratio between xyloglucan and protein being 30:70 or 50:50 and the pH of the solution is 10, and (B) performing Maillard reaction by heating the solution resulting from step (A) at a temperature of 160° C.

In particular, the conjugated products of the invention can be used for the prevention of the proliferation of pathogens in the gastro-intestinal system and the transfer thereof to other systems of the human organism through the narrow intestinal junctions, as well as for the protection of the intestinal mucosa against chemical or physical agents that may reduce the functionality and natural regeneration of the intestinal epithelium and for the reduction of the paracellular flow of pathogens through the intestinal walls.

In addition to the above, the conjugated product of the invention can also be used in the prevention or treatment of damages of the intestinal mucosa and the consequent inflammatory conditions such as diverticulosis and of the early stages of diverticulitis; for the treatment of the symptoms consequent to alimentary allergies (for example lactose intolerance, gluten intolerance etc.); for the prevention and the treatment of digestion disorders (production of gas, meteorism, stomach rumble, flatulence); for the prevention and treatment of damages of the intestinal mucosa deriving from local inflammatory conditions, both of temporary and chronic origin, in particular for the treatment of Crohn's disease, ulcerative colitis, Irritable Bowel Disease (IBD), Irritable Bowel Syndrome (IBS), and enteritis, among others; for the prevention or treatment of chronic gastroesophageal reflux disease (GERD); and for the treatment of diarrhea, optionally in combination with electrolytes for oral rehydration.

In one embodiment of the sixth and/or seventh aspects of the invention, optionally in combination with any of the embodiments provided above or below, the prevention and/or treatment of intestinal disorders is achieved by reducing the permeability and/or the inflammation of intestinal mucosa.

In one embodiment of the sixth and seventh aspects of the invention, optionally in combination with any of the embodiments provided above or below, the conjugated product is used in the treatment of the inflammation of intestinal tract.

In another embodiment of the sixth and/or seventh aspect of the invention, optionally in combination with any of the embodiments provided above or below, the composition is used in the treatment of enteritis.

In another embodiment of the sixth and/or seventh aspect of the invention, optionally in combination with any of the embodiments provided above or below, the composition is used in the treatment of enteritis caused by a pathogenic microorganism.

In still another embodiment of the sixth and/or seventh aspect of the invention, optionally in combination with any of the embodiments provided above or below, the composition is used in the treatment of enteritis caused by E. coli.

In still another embodiment of the sixth and/or seventh aspect of the invention, optionally in combination with any of the embodiments provided above or below, the protein-polysaccharide conjugated product is used in the prevention and/or treatment of an intestinal mucosa inflammatory disorder.

In still another embodiment of the sixth and/or seventh aspect of the invention, optionally in combination with any of the embodiments provided above or below, the protein-polysaccharide conjugated product is used in the prevention or treatment of mucositis.

Mucositis corresponds to the inflammation and ulceration of the mucous membranes lining the digestive tract, usually as an adverse effect of chemotherapy and radiotherapy treatment for cancer. Mucositis can occur anywhere along the gastrointestinal tract, but oral mucositis refers to the particular inflammation and ulceration that occurs in the mouth. Oral mucositis is a common and often debilitating complication of cancer treatment.

5-Fluorouracil (5-FU) is an anticancer drug that is widely used in the treatment of colorectal cancer, and it possesses a chemical structure similar to that of uracil and thymine. The major side effects of 5-FU in humans include myelosuppression, diarrhea, cardiotoxicity, dermatitis, and mucositis. Among these, gastrointestinal mucositis has been reported in approximately 80% of patients who have received cancer treatment by using 5-FU.

Figure 2:
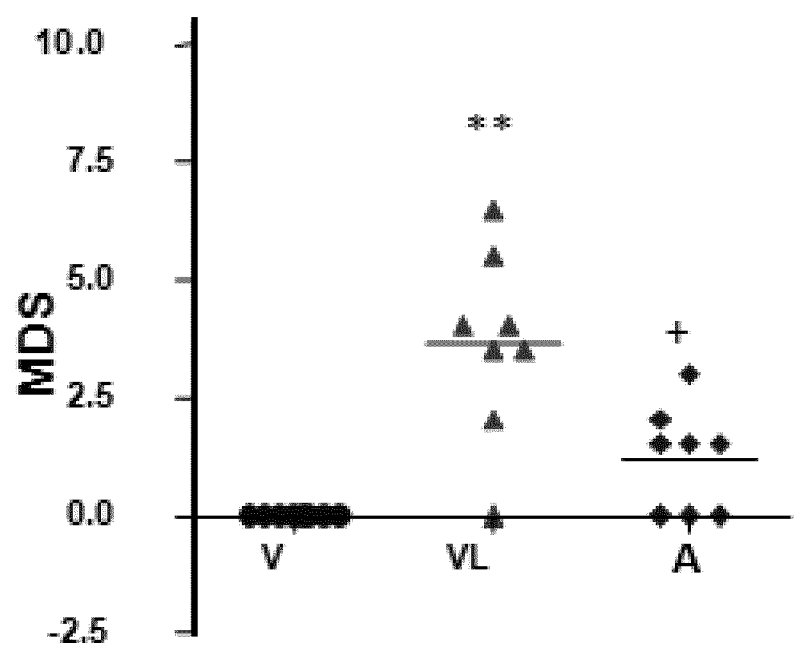
FIG. 2 represents the macroscopic damage score (MDS) for a group of mice which has received water (vehicle, "V"), for a group of mice which has received 5-FU (VL), and for a group of mice which has been orally administered, 7 days before and 5 days after 5-FU, the compound of the invention AT-6 at a dose of 30 mg/kg of mouse (A).
Figure 3:
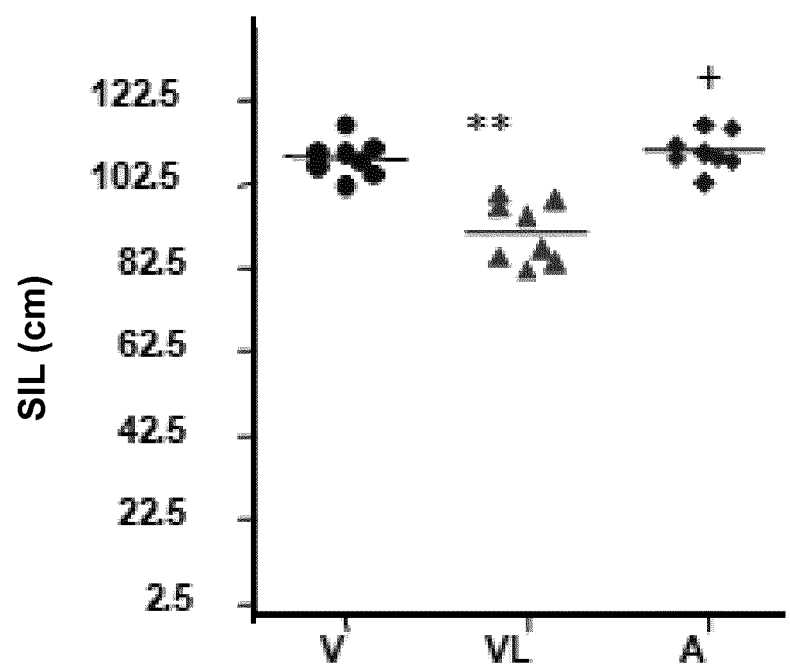
FIG. 3 represents the small intestine length value (SIL), expressed in centimeters, for a group of mice that has received water (vehicle, "V"), for a group of mice which has received 5-FU ("VL"), and for a group of mice which has been orally administered, 7 days before and 5 days after 5-FU, the compound of the invention AT-6 at a dose of 30 mg/kg of mouse (A).
Figure 4:
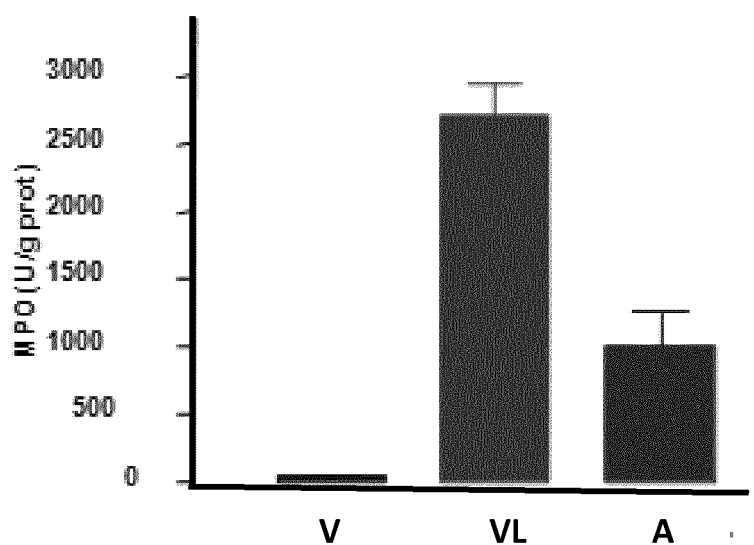
FIG. 4 represents the myeloperoxidase activity (MPO), expressed in units of activity per gram of protein, for a group of mice which has received water (vehicle "V"), for a group of mice which has received 5-FU ("VL"), and for a group of mice which has been orally administered, 7 days before and 5 days after 5-FU, the compound of the invention AT-6 at a dose of 30 mg/kg of mouse (A).

As it is illustrated below, the administration of the conjugated product of the invention, as defined in the second aspect of the invention, surprisingly prevented the intestinal side-effects (mucositis) due to the administration of a chemotherapeutic compound such as 5-FU (FIGS. 2 to 4). In addition, the inventors have found that the preventive effect is achieved even at very low concentrations of the conjugated product of the invention (see FIGS. 5 to 7).

In view of the above, in still another embodiment of the sixth and/or seventh aspect of the invention, optionally in combination with any of the embodiments provided above or below, the protein-polysaccharide conjugated product is used in the prevention and/or treatment of mucositis caused by anticancer therapy, particularly chemotherapy.

Chemotherapy (often abbreviated to chemo and sometimes CTX or CTx) is a category of cancer treatment that uses chemical substances, especially one or more anti-cancer drugs (chemotherapeutic agents) that are given as part of a standardized chemotherapy regimen. Chemotherapy may be given with a curative intent (which almost always involves combinations of drugs), or it may aim to prolong life or to reduce symptoms (palliative chemotherapy). Traditional chemotherapeutic agents are cytotoxic by means of interfering with cell division (mitosis) but cancer cells vary widely in their susceptibility to these agents. To a large extent, chemotherapy can be thought of as a way to damage or stress cells, which may then lead to cell death if apoptosis is initiated. Many of the side effects of chemotherapy can be traced to damage to normal cells that divide rapidly and are thus sensitive to anti-mitotic drugs: cells in the bone marrow, digestive tract, and hair follicles. This results in the most common side-effects of chemotherapy: myelosuppression (decreased production of blood cells, hence also immunosuppression), mucositis (inflammation of the lining of the digestive tract), and alopecia (hair loss).

Illustrative non-limitative examples of chemotherapeutic agents are actinomycin, trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vinblastine, vincristine, vindesine, and vinorelbine, among others.

In one embodiment, the conjugated product defined in the second aspect of the invention and the chemotherapeutic agent are administered separetely.

In one embodiment, the conjugated product defined in the second aspect of the invention and the chemotherapeutic agent are administered simultaneously.

In another embodiment, the conjugated product defined in the second aspect of the invention and the chemotherapeutic agent are administered simultaneously and separetely.

The skilled person is able of determining the amount of chemotherapeutic agent and conjugated product for achieving an efficient anticancer effect without the onset of mucositis. Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Material and Methods

Pea protein was purchased from Roquette Frères and xyloglucan was purchased from DSP Gokyo.

1. Mixtures and Conjugates 1.a. Mixture Xyloglucan:Pea Protein 30:70 (MB 30:70)

14 g of pea protein were dissolved in 500 mL of water. Next, the pH of the solution was adjusted to 10 by the addition of NaOH. Once the pH was adjusted, 6 g of xyloglucan were added to the mixture and more water was added until the total final weight of the solution was 1000 g. The mixture was homogenized using ultra-turrax T25 basic (IKA-WERKE GMBH & CO KG D-79219 Stanfer, Germany).

The whole preparation process was performed at room temperature.

1.b. Mixture Xyloglucan:Pea Protein 50:50 (MB 50:50)

10 g of pea protein were dissolved in 500 mL of water. Next, the pH of the solution was adjusted to 10 by the addition of NaOH. Once the pH was adjusted, 10 g of xyloglucan were added to the mixture and more water was added until the total final weight of the solution is 1000 g. The mixture was homogenized using ultrarrax.

The whole preparation process was performed at room temperature.

1.c. Conjugated Xyloglucan:Protein 30:70 (AT-6) and 50:50 (AT-2)

The resulting mixtures from 1.a. and 1.b. above were atomized in a Mini Spray Dryer B-290, BÜCHI Labortechnik AG (Flawil, Switzerland) at 160° C. until a dry powder was obtained.

1.d. Characterization of Conjugated Xyloglucan:Protein (AT-6)

A complexation study was performed with "AT6" by H-NMR to confirm the covalent bond between pea protein and xyloglucan. Technology DOSY allows analyzing mixtures of compounds by dividing the resonances of compounds with different diffusion coefficients. The spectrum presents a horizontal axis (T2) that identifies the resonance frequencies of the proton (ppm) and a vertical axis that presenting the diffusion parameter.

Three solutions were prepared: one with protein alone, one with xyloglucan alone, and a third one with AT-6. Samples were prepared as follows: 10 mg of either protein, xyloglucan or AT-6 were suspended in 10 mL $D_2O$ and kept under stirring for 48 hours. The resulting suspension was then filtered, and the undissolved material was discarded.

The resulting solutions were subjected to DOSY. NMR spectra were recorded at 298 K in $D_2O$ on a Varian 500 MHz instrument equipped with a pulse-field gradient probe. The HDO residual solvent peak ($\delta$=4.65 ppm) was used as an internal standard. 1H NMR spectra were recorded using solvent suppression pulse sequences (WET). Diffusion-ordered NMR spectroscopy (DOSY) studies were performed using a DgcsteSL pulse sequence, optimizing experimental parameters according to the sample under investigation. Diffusion gradients were progressively incremented over 30 steps, varying the gradient strength from 1.8 to 50.0 gauss/cm. 16 Transients were acquired for each increment, with a diffusion-gradient length of 4 ms and diffusion delays of 400 ms.

The DOSY NMR analysis on the soluble fractions of the three samples returned the following results, as far as the self-diffusion coefficient ranges are concerned:

Sample A (Pea): $1\text{-}3\times10^{-1\circ}$ $(m^2\ s^{-1})$
Sample B (Tamarind): $0.08\text{-}0.1\times10^{-1\circ}$ $(m^2\ s^{-1})$
Sample C (Pea+Tamarind): $0.1\text{-}0.3\times10^{-1\circ}$ $(m^2\ s^{-1})$ These results indicated that the Maillard reaction between a polysaccharide (xyloglucan) and protein (pea protein) provides a conjugate wherein protein and polysaccharide are covalently bound.

2. Animals 8 groups of 8 male Wistar rats (Janvier S. A., Le Genest St. Isle, France) weighing 200-225 g were made. The protocol consisted of a preventive oral administration of the mixture or conjugated product resulting from sections 1.a. to 1.d. above, 2 h before intraperitoneally administering 250 µL of sterile saline (NaCl 0.9%) containing or not (control) 1 mg/kg of lipopolysacharide (LPS) from E. coli (Sigma Aldrich, L2630). (This dose of LPS has been previously shown to alter intestinal permeability and to release pro-inflammatory cytokines in the mucosa):

1 group as the control group (vehicle)–no LPS;
1 group as the positive group (vehicle+LPS);
1 group AT 6 at 30:70=complex 30% of Xyloglucan and 70% of Pea protein;
1 group AT2 at 50:50=complex 50% of xyloglucan and 50% of Pea Protein;
1 group MB 30:70=mixture with 30% of xyloglucan and 70% of pea protein; and
1 group MB 50:50=mixture with 50% of Xyloglucan and 50% of Pea protein The dose of the mixture or conjugate, administered to each animal, was adjusted according to 250 mg of the mixture or conjugate per kg of animal, and the resulting amount was diluted in 1 mL of water.

3. Evaluated Parameters 3.1. Gut Permeability

Six hours after LPS administration, the rats were sacrificed by cervical dislocation and the proximal part of the jejunum was removed. Jejunal strips were mounted in Ussing-type chambers (Physiologic Instruments, San Diego, Calif.). Both sides of each jejunal layer were bathed in Krebs-Henseleit buffer (Sigma) and oxygenated on a maintained temperature of 37° C. After 15 min for equilibrium, 1 ml of the buffer solution was replaced with physiological saline and 500 µl of FITC-dextran (4000 MW, 0.022 g/ml, Sigma) on mucosal side of each chamber. After 60 min fluorescence intensity was measured.

3.2. Myeloperoxidase (MPO) Activity

MPO activity, a marker of polymorphonuclear neutrophil primary granules, was determined in proximal jejunum tissues, according to a modified method of Bradley et al., (1982). After sacrifice, jejunal samples were removed and snap frozen until the MPO activity determination. Briefly, the jejunal segments were grind by using a Polytron, in presence of 1.5 ml of a cationic surfactant releasing MPO hexadecyltrimethylammonium bromide (HTAB) before being submitted to 3 cycles of freezing-thawing, and centrifugation, (10 000 rpm at 4° C., during 15 min). Homogenates were sonicated and centrifuged (10 000 rpm at 4° C., during 15 min) another time. Supernatants were discarded and pellets were resuspended in hexadecyltrimethylammonium bromide (HTAB) that releases MPO. These suspensions were sonicated on ice, and then centrifuged at 10000 rpm at 4° C. for 15 min, another time. Pellets were discarded and supernatants were assayed for MPO activity spectrophotometrically (absorbance evaluation at 450 nm) and protein measurements. Protein concentration was determined by the method of Lowry (Bio Rad Detergent Compatible Protein Assay, BIO Rad, Ivry-France), using the Kit BCA Uptima Interchim (absorbance at 570 nm). MPO activity was expressed as MPO Units/g of protein.

3.3. Mucoadhesion

Mixtures 50:50 and 30:70 (xyloglucan:protein) prepared as disclosed in sections 1.a. and 1.b. above were submitted to a Maillard reaction in an atomizer (Mini Spray Dryer B-290, BÜCHI Labortechnik AG (Flawil, Switzerland) at 160° C.

The parameter measured in the tested samples was the work of adhesion parameter (mN*mm), calculated as the area under the force vs. displacement curve using a TA-XTplus Texture Analyzer device, in tension mode. The method is based on the measurement of the force needed to detach the conjugate, previously applied on a lower platform of the device, from a commercial porcine mucin (dispersion at 20%) layer spread on a lower surface from a cylindrical metal probe (diameter of 20 mm). Under these conditions, the probe scrolls down at a constant speed of 0.5 mm/s to contact with the platform comprising the conjugate to be tested. In order to unify the measurements, a constant pre-charge of 1.5 N is applied for 60 seconds. Next, the probe is removed at a constant speed of 2 mm/s, and the maximum force of detaching is registered (mN) as well as the distance gone until reaching the maximum force (mm). The "work of mucoadhesion" is expressed as the force multiplied by the distance (mN*mm).

Results

1. Comparative Effect on Jejuna Permeability

LPS IP administration induced a strong increase in jejuna permeability (514.2±39.7 vs 48.2±8.7 pmol/h/cm$^2$ in controls) which was significantly prevented by the oral treatment of AT2 and AT6 (384.4±20.3, 169.1±15.4 vs 514.5±39.7 pmol/h/cm$^2$ in LPS group respectively).

Surprisingly, it was found, that the conjugation of protein to xiloglucan conferred a synergistic effect, being a substantial reduction in permeability:

TABLE 1

| Sample | Permeability (pmol/h/cm$^2$) |
|---|---|
| LPS | 514.2 ± 39.7 |
| AT2 50:50 | 384.4 ± 20.3 |
| AT6 30:70 | 169.1 ± 15.4 |
| MB 50:50 | 430.0 ± 31.8 |
| MB 30:70 | 459.9 ± 20.1 |

As it is derived from Table 1, mixing both components (MB 50:50 and MB 30:70) no significant reduction in gut permeability is achieved. However, when both components are conjugated (AT2 and AT6), a substantial reduction in gut permeability of at least 25% is achieved.

In case of AT6, a 3-fold reduction in gut permeability is achieved whereas MB 30:70 (wherein protein and xyloglucan are not conjugated) provides a 1-fold reduction.

2. Comparative Effects on Myeloperoxidase Activity

LPS IP administration induced a marked increase in MPO activity (903.8±61.9 vs 329.3±43.4 MPO Units/g protein in controls).

AT6 treatment significantly prevented the inflammatory effect in the jejuna mucosa induced by LPS administration:

TABLE 2

| Sample | Permeability (pmol/h/cm$^2$) |
|---|---|
| LPS | 903.8 ± 61.9 |
| AT6 30:70 | 737.1 ± 44.7 |
| MB 30:70 | 943.9 ± 45.1 |

3. Mucoadhesion Profile

A 3-fold reduction in mucoadhesivity was observed when protein was conjugated to xyloglucan, when compared with xyloglucan alone (see FIG. 1). Therefore, conjugates xyloglucan-pea protein of the invention show less mucoadhesion than xyloglucan alone.

That is, the covalent binding of the protein, negatively affected xyloglucan mucoadhesion. In spite of this worst mucoadhesion profile, remarkable improvement in gut permeability and inflammation prevention were found in the in-vivo experiments reported above.

Efficiency of the Conjugated Product of the Invention in Chemotherapy-Induced Mucositis I. Material and Methods I.1. Animals Male Wistar rats (200-225 g) were used. In a first series of experiments animals were treated by some compounds 7 days before and 5 days after an intraperitoneal (IP) injection of 5-FU (150 mg/kg). In a second series, tested compound AT-6 (which were obtained as disclosed above) was administered 24 h before and 5 days after 5-FU administration.

II.2 Evaluated Parameters

II.2.1. Length of the Small Intestine and Macroscopic Damage Scores (MDS)

At the 5th day after 5-FU administration animals were sacrificed and the length of the small intestine was measured as an index of inflammatory tone. The macroscopic damage scores were determined according to a modified Wallace index.

III. Experimental Design

First Series of Experiments (Preventive and Curative Protocol)

5 groups of 8 male Wistar rats (Janvier S. A., Le Genest St. Isle, France) weighing 200-225 g were used in this series. The protocol consisted of a preventive and curative oral treatment with AT6 compound 7 days before and days after 5-FU administration. At the end of the treatments after sacrifice the macroscopic damage scores were established, the length of the colon measured and the MPO activity measured from an isolated jejuna segment.

The experimental groups were performed as follows:
1 group as the control group (vehicle; water 1 ml PO),
1 group as the positive group (vehicle PO+5-FU 150 mg/kg IP,
1 group AT6 30 mg/kg PO++5-FU 150 mg/kg IP (following the protocol described in the previous paragraph).

Second Series of Experiments (Curative Protocol)

8 groups of 8 male Wistar rats (Janvier S. A., Le Genest St. Isle, France) weighing 200-225 g were used in this series. The protocol consisted of a curative oral treatment based on the administration of AT6 24 h before and 5 days after 5-FU administration. At the end of the treatments after sacrifice the macroscopic damage scores were established, and the length of the small intestine and the MPO activity were measured from an isolated jejunal segment.

The experimental groups were be performed as follows:
1 group as the control group (vehicle; water 1 ml PO),
1 group as the positive group (vehicle PO+5-FU 150 mg/kg IP,
1 group AT6 30 mg/kg PO+5-FU 150 mg/kg IP (following the protocol described in the previous paragraph),
1 group AT6 20 mg/kg PO+5-FU 150 mg/kg IP (following the protocol described in the previous paragraph), and,
1 group AT6 10 mg/kg PO+5-FU 150 mg/kg IP (following the protocol described in the previous paragraph).

III. Results

First series of experiments: effect on macroscopic damage scores, small intestine length and MPO activity 5-FU significantly ($p<0.01$) increased the macroscopic damage score determined in the small intestine. The AT6 30 mg/kg PO treatment significantly prevented the 5-FU effect ($p<0.01$; $p<0.05$ respectively (FIG. 2).

On the other hand, 5-FU significantly ($p<0.01$) decreased the small intestine length, reflecting inflammatory tone. The AT6 30 mg/kg PO treatment significantly ($p<0.05$) prevented the 5-FU effect (FIG. 3).

5-FU significantly ($p<0.01$) increased the MPO activity determined in the small intestine. The AT6 30 mg/kg PO treatment significantly prevented the 5-FU effect (FIG. 4).

Figure 5:
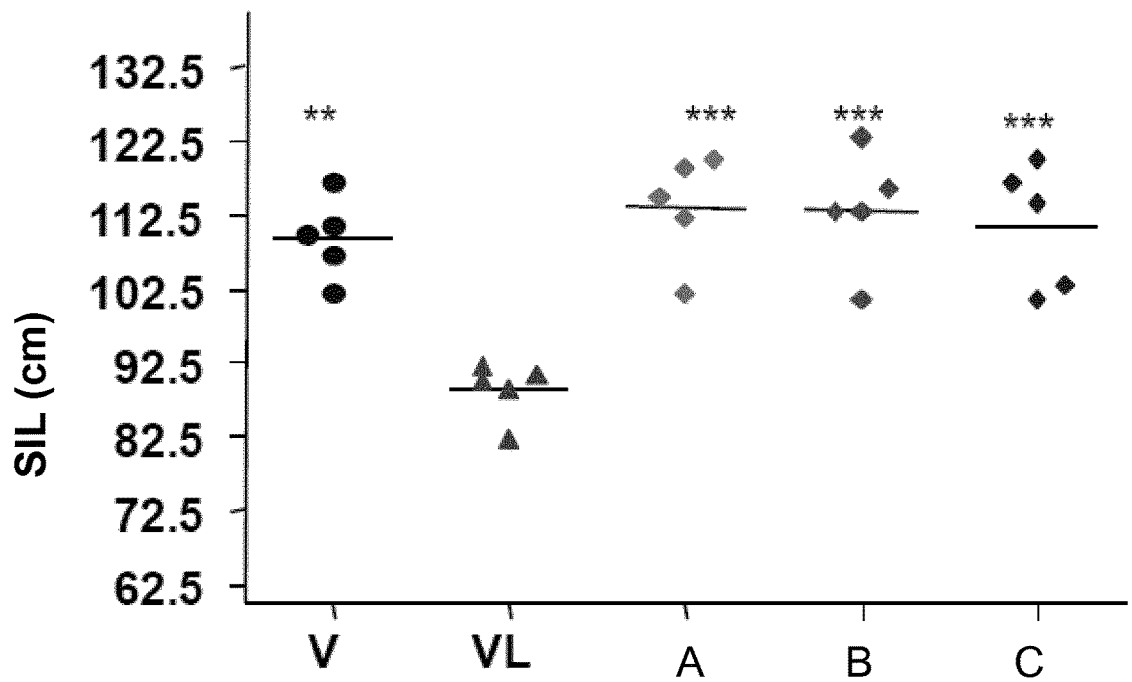
FIG. 5 represents the small intestine length value (SIL), expressed in centimeters, for a group of mice which has received water (vehicle, "V"), for a group of mice which has received 5-FU (VL), and for a group of mice which has been orally administered, 24 hours before and 5 days after 5-FU, the compound of the invention AT-6 at a dose of 30 mg/kg (A), of 20 mg/kg (B) and of 10 mg/kg of mouse (C).

Second series of experiments: effect on macroscopic damage scores, small intestine length and MPO activity 5-FU significantly ($p<0.01$ and $p<0.001$) decreased the small intestine length, reflecting inflammatory tone. All treatments applied, strongly reversed the 5-FU effect (FIG. 5).

Figure 6:
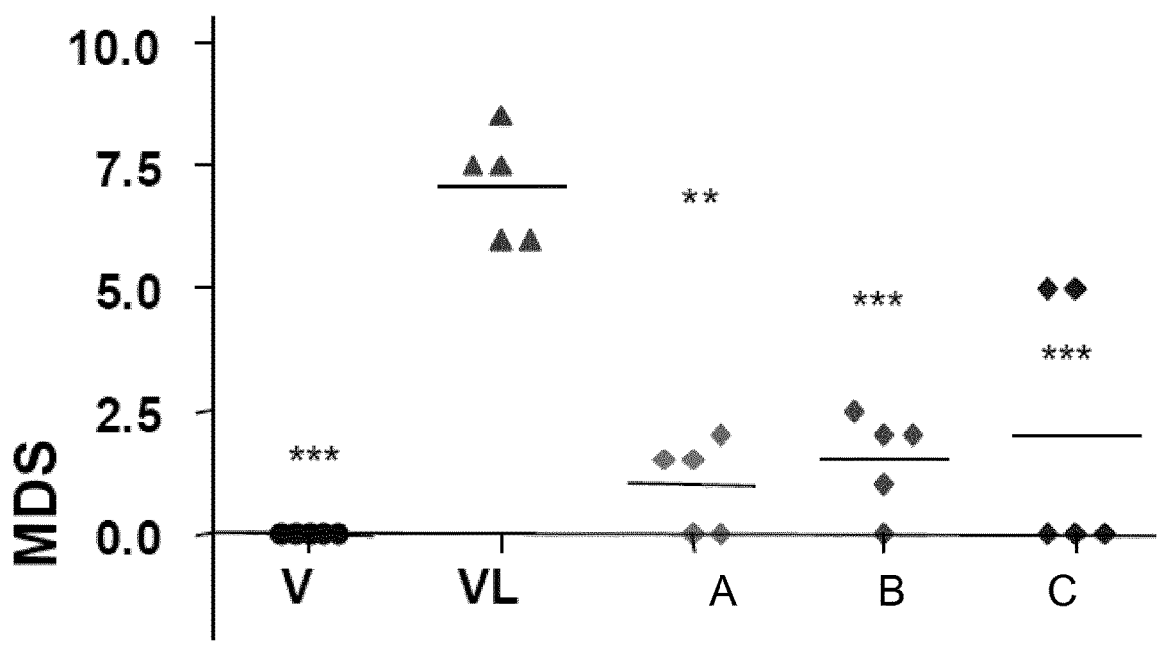
FIG. 6 represents the macroscopic damage score (MDS) for a group of mice which has received water (vehicle, "V"), for a group of mice which has received 5-FU (VL), and for a group of mice which has been orally administered, 24 hours before and 5 days after 5-FU, the compound of the invention AT-6 at a dose of 30 mg/kg (A), of 20 mg/kg (B) and of 10 mg/kg of mouse (C).

5-FU significantly ($p<0.01$) increased the macroscopic damage score determined in the small intestine. All treatments applied, strongly reversed the 5-FU effect on MDS (FIG. 6)

Figure 7:
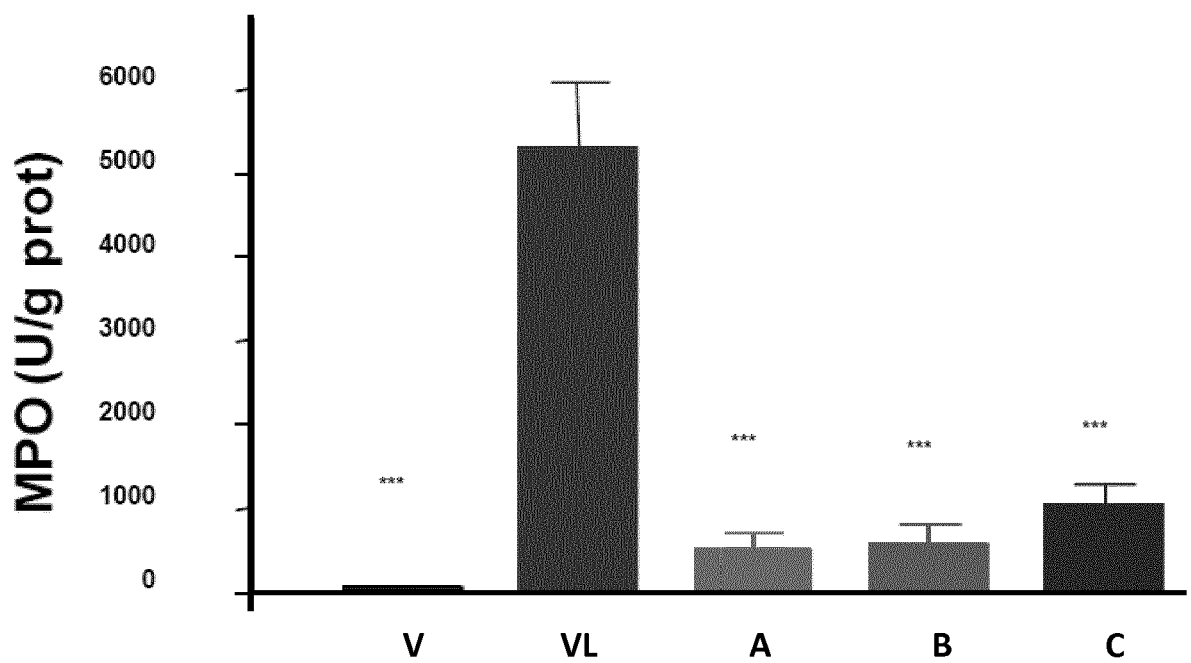
FIG. 7 represents the myeloperoxidase activity (MPO), expressed in units of activity per gram of protein, for a group of mice which has received water (vehicle, "V"), for a group of mice which has received 5-FU (VL), and for a group of mice which has been orally administered, 24 hours before and 5 days after 5-FU, the compound of the invention AT-6 at a dose of 30 mg/kg (A), of 20 mg/kg (B) and of 10 mg/kg of mouse (C).

5-FU strongly increased the MPO activity determined in the small intestine. All treatments prevented the 5-FU-induced effect on MPO (FIG. 7)

IV Conclusion

These data show the clear efficacy of the conjugated product of the invention against 5-FU induced gut damages. It is noteworthy that the beneficial effects were obtained both in the preventive and curative treatments, highlighting that the local protective effect of these compounds starts rapidly after their oral administration.

Taking into account the results obtained from the first and second series of experiments, the beneficial effects observed are strongly related to the presence of AT6. In the "curative" protocol AT6 alone exhibit a strong efficacy even in the lowest dose. These results are promising for the use of this compound against side effects of chemotherapy.

REFERENCES CITED IN THE APPLICATION

WO2006131262
WO2015158771
Bradley P. P. et al., "Measurement of cutaneous inflammation: estimation of neutrophil content with an enzyme marker", J. Invest. Dermatol., 1982, v. 78(3), pages 206-209.

The invention claimed is:

1. A method for the prevention and/or treatment of gastrointestinal disorders in a subject, the method comprising administering a therapeutically effective amount of a pea protein xyloglucan conjugated product to a subject in need thereof,
wherein the pea protein is conjugated to xyloglucan,
wherein the weight ratio between the xyloglucan and the pea protein is 30:70 to 50:50, and
wherein the protein-xyloglucan conjugated product is obtainable by a process comprising the steps of:
(A) preparing a mixture comprising pea protein, xyloglucan, and an appropriate polar solvent, wherein
the weight ratio between the xyloglucan and the pea protein is 30:70 to 50:50, and
the pH of the solution is comprised from 8.0 to 10.5, and
(B) performing a Maillard reaction by heating the solution resulting from step (A) at an appropriate temperature for the necessary period of time to conjugate the pea protein and the xyloglucan.

2. The method as claimed in claim 1, wherein the prevention and/or treatment of intestinal disorders is achieved by reducing the gut permeability and/or by reducing the inflammation of jejuna mucosa.

3. The method as claimed in claim 1, wherein the gastrointestinal disorder is an intestinal mucosa inflammatory disorder.

4. The method as claimed in claim 3, wherein the disorder is mucositis or is caused by anti-cancer therapy.

5. The method as claimed in claim 4, wherein the anti-cancer therapy is chemotherapy.

6. The method as claimed in claim 1, wherein the weight ratio between the xyloglucan and the pea protein is 30:70.

7. A method for the prevention and/or treatment of an intestinal mucosa inflammatory disorder caused by an anti-cancer treatment in a subject, the method comprising administering a therapeutically effective amount of a combination therapy comprising a pea protein-xyloglucan conjugated product with the anti-cancer treatment to a subject in need thereof,
wherein the pea protein is conjugated to xyloglucan,
wherein the weight ratio between the xyloglucan and the pea protein is 30:70 to 50:50, and wherein the protein-xyloglucan conjugated product is obtainable by a process comprising the steps of:
(A) preparing a mixture comprising pea protein, xyloglucan, and an appropriate polar solvent, wherein the weight ratio between the xyloglucan and the pea protein is 30:70 to 50:50, and
the pH of the solution is comprised from 8.0 to 10.5, and
(B) performing a Maillard reaction by heating the solution resulting from step (A) at an appropriate temperature for the necessary period of time to conjugate the pea protein and the xyloglucan.

8. The method as claimed in claim 7, wherein the weight ratio between the xyloglucan and the pea protein is 30:70.

* * * * *